United States Patent
Rabe

(10) Patent No.: US 10,238,582 B2
(45) Date of Patent: Mar. 26, 2019

(54) APPARATUS AND METHODS FOR MODIFYING KERATINOUS SURFACES

(71) Applicant: The Procter & Gamble Company, Cincinnati, OH (US)

(72) Inventor: Thomas Eliott Rabe, Baltimore, MD (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 15/704,541

(22) Filed: Sep. 14, 2017

(65) Prior Publication Data
US 2018/0000697 A1    Jan. 4, 2018

Related U.S. Application Data

(60) Division of application No. 14/858,300, filed on Sep. 18, 2015, now abandoned, which is a continuation-in-part of application No. 14/736,507, filed on Jun. 11, 2015, now Pat. No. 9,925,362, and a continuation-in-part of application No. 14/736,524, filed on Jun. 11, 2015, now Pat. No. 9,924,875, and a continuation-in-part of application No. 14/736,534, filed on Jun. 11, 2015, now Pat. No. 9,928,591, and a continuation-in-part of application No. 14/736,551, filed on Jun. 11, 2015, and a continuation-in-part of application No. 14/736,563, filed on Jun. 11, 2015, now abandoned, and a continuation-in-part of application No. 14/736,584, filed on Jun. 11, 2015, now Pat. No. 9,522,101, and a continuation-in-part of application No. 14/807,140, filed on Jul. 23, 2015, and a continuation-in-part of application No. 14/807,198, filed on Jul. 23, 2015, and a continuation-in-part of application No. 14/807,231, filed on Jul. 23, 2015, now Pat. No. 9,949,552, and a continuation-in-part of application No. 14/807,257, filed on Jul. 23, 2015, now abandoned, and a continuation-in-part of application No. 14/807,297, filed on Jul. 23, 2015, and a continuation-in-part of application No. 14/807,360, filed on Jul. 23, 2015, now Pat. No. 9,955,769.

(51) Int. Cl.
| | | |
|---|---|---|
| A61K 8/02 | (2006.01) | |
| A61Q 17/04 | (2006.01) | |
| A61K 8/29 | (2006.01) | |
| A61K 8/27 | (2006.01) | |
| A61K 8/19 | (2006.01) | |
| A61K 8/81 | (2006.01) | |
| A61K 8/25 | (2006.01) | |
| A61K 8/85 | (2006.01) | |
| A61Q 1/02 | (2006.01) | |
| A61M 5/20 | (2006.01) | |
| A61M 5/30 | (2006.01) | |
| A61M 37/00 | (2006.01) | |

(52) U.S. Cl.
CPC ............ *A61K 8/0241* (2013.01); *A61K 8/022* (2013.01); *A61K 8/19* (2013.01); *A61K 8/25* (2013.01); *A61K 8/27* (2013.01); *A61K 8/29* (2013.01); *A61K 8/8111* (2013.01); *A61K 8/8123* (2013.01); *A61K 8/85* (2013.01); *A61M 5/2053* (2013.01); *A61M 5/30* (2013.01); *A61Q 1/02* (2013.01); *A61Q 1/025* (2013.01); *A61Q 17/04* (2013.01); *A61K 2800/413* (2013.01); *A61K 2800/91* (2013.01); *A61M 5/3015* (2013.01); *A61M 2037/0007* (2013.01)

(58) Field of Classification Search
CPC .................................. A61N 1/44; A61M 37/00
See application file for complete search history.

(56) References Cited

U.S. PATENT DOCUMENTS

| | | | |
|---|---|---|---|
| 5,630,796 | A | 5/1997 | Bellhouse et al. |
| 6,312,124 | B1 | 11/2001 | Esormeaux |
| 7,648,364 | B2 | 1/2010 | Dauga |
| 7,890,152 | B2 | 2/2011 | Edgar |

(Continued)

FOREIGN PATENT DOCUMENTS

| | | |
|---|---|---|
| FR | 2933585 B1 | 10/2011 |
| JP | 2006297691 A | 11/2006 |

(Continued)

OTHER PUBLICATIONS

All Office Actions from U.S. Appl. No. 14/858,300, filed Sep. 18, 2015.
U.S. Appl. No. 14/858,300, filed Sep. 18, 2015, Thomas Elliot Rabe.
U.S. Appl. No. 14/858,357, filed Sep. 18, 2015, Thomas Elliot Rabe.
U.S. Appl. No. 14/858,367, filed Sep. 18, 2015, Thomas Elliot Rabe.
U.S. Appl. No. 14/858,390, filed Sep. 18, 2015, Thomas Elliot Rabe.
Search Report; PCT/US2016/036780; dated Sep. 20, 2016; 13 Pages.

(Continued)

*Primary Examiner* — Kyle A Purdy
(74) *Attorney, Agent, or Firm* — Melissa G. Krasovec

(57) ABSTRACT

An apparatus and method for depositing a particulate containing composition onto mammalian skin such that when the particles contact the mammalian skin they have a momentum defined by $\rho vr$, which is within the range of about 0.1 kg/ms $\leq \rho vr \leq$ about 12.0 kg/ms. The particles can be in the range of from about 10 nanometers to about 10 micrometers, in size. And the particles may be selected from the group consisting of titanium dioxide, zinc oxide, iron oxide, polyethylene, polypropylene, polyethylene terephthalate, polycarbonate, polyvinyl chloride, glass, silica and mixtures thereof. The particles are imbedded below the first layer of dead skin cells in the stratum corneum but they do not pass all the way through the stratum corneum into the living cells of the epidermis or dermis layers of the skin.

12 Claims, No Drawings

(56) References Cited

U.S. PATENT DOCUMENTS

| | | |
|---|---|---|
| 8,007,062 B2 | 8/2011 | Edgar |
| 8,027,505 B2 | 9/2011 | Edgar |
| 8,184,901 B2 | 5/2012 | Edgar |
| 8,231,292 B2 | 7/2012 | Rabe |
| 8,695,610 B2 | 4/2014 | Samain |
| D750,772 S | 2/2016 | Rabe |
| D750,225 S | 3/2016 | Rabe |
| 2003/0060810 A1 | 3/2003 | Syrowicz |
| 2008/0194971 A1 | 8/2008 | Edgar |
| 2009/0025747 A1 | 1/2009 | Edgar |
| 2010/0224205 A1 | 9/2010 | Mitra |
| 2010/0224209 A1 | 9/2010 | Rabe |
| 2010/0224210 A1 | 9/2010 | Rabe |
| 2010/0224211 A1 | 9/2010 | Samain |
| 2011/0129283 A1 | 6/2011 | Samain |
| 2011/0155161 A1 | 6/2011 | Samain |
| 2011/0159463 A1 | 6/2011 | Rabe |
| 2011/0162673 A1 | 7/2011 | Samain |
| 2013/0071319 A1 | 3/2013 | Boyden et al. |
| 2015/0094647 A1* | 4/2015 | Kalghatgi ............ A61M 37/00 604/23 |
| 2015/0360015 A1 | 12/2015 | Rabe |
| 2015/0360016 A1 | 12/2015 | Rabe |
| 2015/0360017 A1 | 12/2015 | Rabe |
| 2015/0360018 A1 | 12/2015 | Baker |
| 2015/0360019 A1 | 12/2015 | Clancy |
| 2015/0360020 A1 | 12/2015 | Wu |
| 2016/0022006 A1 | 1/2016 | Rabe |
| 2016/0022008 A1 | 1/2016 | Rabe |
| 2016/0022009 A1 | 1/2016 | Rabe |
| 2016/0022010 A1 | 1/2016 | Rabe |
| 2016/0022011 A1 | 1/2016 | Rabe |
| 2016/0022972 A1 | 1/2016 | Rabe |

FOREIGN PATENT DOCUMENTS

| | | |
|---|---|---|
| WO | WO9528912 A1 | 11/1995 |
| WO | WO2004060262 A2 | 7/2004 |
| WO | WO2009036876 | 3/2009 |
| WO | WO2010004531 | 1/2010 |

OTHER PUBLICATIONS

Kendall M et al: "Intradermal ballistic delivery of micro-particles into excised human skin for pharmaceutical applications", Journal of Biomechanics, Pergamon Press, New York, NY, US, vol. 37. No. 11, Nov. 1, 2004 (20G4-11-O1), pp. 1733-1741, XPO04573459. (9 Pages).

* cited by examiner

APPARATUS AND METHODS FOR MODIFYING KERATINOUS SURFACES

FIELD OF THE INVENTION

This invention relates to an apparatus and method for applying a composition to the surface of human or animal skin at high velocity in order to embed the composition into the stratum corneum layers of the skin. The composition may be particulate, fluid or combinations of these.

BACKGROUND OF THE INVENTION

The stratum corneum of human and animal skin is the outermost layer of the epidermis, consisting of dead cells known as corneocytes. These stratum corneum is composed of 15-20 layers of flattened cells with no nuclei and cell organelles. These layers are continually being exfoliated and replaced by new layers of dead cells. Depending on the area of the body the time for complete turnover of all layers of the stratum corneum is normally 2-4 weeks. There are many products that are designed to be applied to the surface (top layer) of the stratum corneum. These are primarily skin care and cosmetic products. Within these categories of products one benefit area that is important and has led to continual innovation is that of durability. Extending the length of time that a product remains on the skin is desirable for both cosmetic effect as well as for skin protection products like sunscreens. However, there are many drawbacks to the current approaches to creating long wearing topical products. The first is that they usually utilize adhesive polymers which impart a tight or tacky feel to the skin. Additionally they are susceptible to being dissolved by contact with water, sweat and sebum. Furthermore even the longest wearing, most durable products rarely last for more than 24 hours due to the fact that they are only attached to the top layer of the stratum corneum and once this layer is exfoliated the product or film is removed from the body along with it.

These and other deficiencies of the existing skin care treatments require improvement. The performance and consumer acceptance of skin care regimens will be greatly improved by addressing the aforementioned shortcomings.

SUMMARY OF THE INVENTION

The present invention relates to apparatuses and methods for depositing a particulate containing composition onto mammalian skin such that when the particles contact the mammalian skin they have a momentum defined by ρvr within the range of about 0.1 kg/ms≤ρvr≤about 12.0 kg/ms. The particles are in the range of from about 10 nanometers to about 10 micrometers, preferably from about 200 nanometers to about 10 micrometers, in size. And in one embodiment the particles are selected from the group consisting of titanium dioxide, zinc oxide, iron oxide, polyethylene, polypropylene, polyethylene terephthalate, polycarbonate, polyvinyl chloride, glass, silica and mixtures thereof.

In a preferred embodiment, the particles are imbedded below the first layer of dead skin cells in the stratum corneum and they do not pass all the way through the stratum corneum into the living cells of the epidermis or dermis layers of the skin. More specifically, the particles are injected into the stratum corneum but no deeper than from about 10 micrometers to about 40 micrometers into the mammalian skin. The particles that are injected into the stratum corneum may remain there for at least one day. And the particles are injected into the stratum corneum to achieve a skin benefit selected from the group consisting of a cosmetic, UV protection, skin radiance and mixtures thereof.

The present invention seeks to alleviate the tradeoffs of wear versus feel by extending the duration of a cosmetic benefit by embedding a product into the stratum corneum rather than have the product attached to the outermost layer of the stratum corneum. The product is only meant to reside in the stratum corneum layers and not beyond it into nucleus containing cells. Thereby the product is not a permanent part of the skin, and will eventually be depleted through the natural exfoliation process. The length of time the product resides in the skin will depend on the number of layers deep it resides in the stratum corneum and the rate of turnover for that part of the body.

DETAILED DESCRIPTION OF THE INVENTION

The present invention may be understood more readily by reference to the following detailed description of illustrative and preferred embodiments. It is to be understood that the scope of the claims is not limited to the specific compositions, methods, conditions, devices, or parameters described herein, and that the terminology used herein is not intended to be limiting of the claimed invention. Also, as used in the specification, including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent basis "about," it will be understood that the particular values form another embodiment. All ranges are inclusive and combinable.

The present invention pertains to a device that accelerates solid particulates to a velocity capable of penetrating into but not beyond the layers of the human stratum corneum. Methods of accelerating particles include various ways of incorporating the particles into a high velocity gaseous stream. Light gasses including helium, nitrogen and oxygen can be utilized. One method of energizing gas is by compressing it. When the gas is released, the resulting pressure drop from the compressed state to atmospheric pressure results in acceleration of the gas and any entrained particles. The velocity of the gas is determined by the pressure differential and the and flow path dimensions. The pressure differential on either side of a gas nozzle, and the geometry of the nozzle can be designed to create a specific gas velocity profile.

Particles can be entrapped in a high velocity gaseous stream by preloading a "dose" of particulates that are delivered as a single shot or metered into the gaseous stream over time. The desired velocity profile of the gas and entrapped particulates should be adjusted based on the particle size and specific gravity in order to create the appropriate momentum required to penetrate—but not surpass—the layers of the stratum corneum. For the purposes of this invention, the multiplicative factor of ρvr will be used as a measure of the momentum and thus the predicted penetration depth into the stratum corneum. Importantly ρvr can control the gas velocity profile accurately enough to ensure that the particles cannot penetrated beyond the stratum corneum.

There has been prior development of devices that are designed to inject particles into the skin beyond the stratum corneum, primarily for drug delivery. Much of the invention of these devices is to find ways to efficiently drive the particles through and beyond the stratum corneum. The objective of the present invention is very different as it is intended to be designed in a manner that ensures that no particles pass beyond the stratum corneum layers. This ensures that the particles reside in the skin temporarily, not permanently.

Gas driven apparatus for accelerating particles are known in the art. For example, U.S. Pat. No. 7,618,394, Bellhouse et al, discloses a device that creates supersonic gas flow for therapeutic particle delivery. In this invention the device is designed to create accelerate the particles to a high enough velocity (dependent on the particle size and specific gravity) to penetrate between 100-500 microns beneath the skin. This is critical for the treatment or drug to be bioavailable. However, this approach would not be practical for temporary administration needs like that of cosmetic or skin protection effects.

Particle momentum can be directly correlated to the depth of penetration into human and animal skin. Particle momentum is essentially a function on the density ($\rho$), velocity (v), and size, or radius (r). Prior experimentation documented in "Comparison of the Transdermal Ballistic Delivery of Micro-particles into Human and Porcine Skin", M. A. F. Kendall et al, Engineering in Medicine and Biology Society, 2001, Proceedings of the 23rd Annual International Conference of the IEEE (Volume:3), pp 2991-2994 shows the relationship between particle momentum ($\rho$vr) and penetration depth into human and porcine cadaver skin. Based on this experimentation velocity requirements for a specific particle (in this gas gold micro beads) were determined in order to have sufficient momentum to penetrate past the stratum corneum. The results of these penetration studies formed the bases for the required applicator design for U.S. Pat. No. 7,618,394, Bellhouse et al.

The present apparatuses and methods are designed to operate at different parameters than the prior art. Instead of designing a delivery system capable of creating particle momentum high enough to penetrate beyond the stratum corneum, which requires a $\rho vr \geq$ approximately 8 kg/ms depending on the stratum corneum thickness, the present invention is designed to accelerate particles within the range of $0.1 \leq \rho vr \leq 12.0$. Particles within the range of $0.1 \leq \rho vr \leq 12.0$ will theoretically have a penetration depth into human skin less than the thickness of the stratum corneum, depending on the area of the body.

The thickness of the stratum corneum varies by area of the body as well as from individual to individual. However, for the purposes of the current invention it is necessary to establish a thickness to which the device is designed against. There are numerous studies of the thickness of human stratum corneum. One of the more comprehensive studies which will be referenced here is "In Vivo Estimation of Stratum Corneum Thickness from Water Concentration Profiles Obtained with Ramen Spectroscopy," M. Egawa et al, Acta Derm Venereologica, vol. 87, pp 4-8. In this study it the mean apparent thickness of the stratum corneum of 15 subjects was found to be 16.8 microns with a standard deviation of 2.84 microns for the cheek, 21.8 microns with a standard deviation of 3.63 microns for the upper forearm, 22.6 microns with a standard deviation of 4.33 microns for the forearm, and 29.3 microns with a standard deviation of 6.84 microns for the back of the hand. Based on these average thicknesses the device of the present invention will need to be varied to account for the appropriate $\rho vr$ for each area of the body.

Based on known penetration studies referenced in the "Comparison of the Transdermal Ballistic Delivery of Micro-particles into Human and Porcine Skin", M. A. F. Kendall et al, Engineering in Medicine and Biology Society, 2001, Proceedings of the 23rd Annual International Conference of the IEEE (Volume:3), pp 2991-2994, the relationship between the $\rho vr$ of the given particle and the corresponding penetration can be predicted. Based on this data, in order to ensure that the particle does not penetrate beyond the stratum corneum for the areas of the body with thin stratum corneum like the cheek, the device of the current invention is designed to deliver a $\rho vr$ between 0.1 and 12.0 kg/ms.

The particles of interest for the present invention are chosen from a list of organic and inorganic cosmetic grade pigment particles, sunscreen particles, particles encapsulating skin actives, polymeric particles, oil absorbing particles, water absorbing particles, and antibacterial particles. In one embodiment of the invention the particulates delivered into the stratum corneum are inorganic metal oxides. Titanium dioxide and iron oxides are of particular interest. This is because they are FD&C approved for contact with human skin.

In one embodiment the present invention creates long lasting cosmetic benefit of coloration. Conventional make-ups and concealers utilize a combination of titanium dioxide and iron oxides to cover skin discolorations but their cosmetic benefit only lasts for hours, not days since they are applied to the surface of the skin. Furthermore they induce a negative skin feel. One benefit of the present invention is that the cosmetic benefits will last for multiple days, depending on how many layers into the stratum corneum the particles are embedded. Cosmetic grade pigments preferred for use herein are most commonly between 200 nanometers and 10 microns in particle size. Below 200 nanometers they become less opaque as the optimal light scatter for a particle is ½ the wavelength of light. Since the visible wavelengths of light are between 400 and 700 nanometers below 200 nanometers the light scatter and hence the opacity of the particle decreases.

In another embodiment of the present invention a much smaller particle size of either titanium dioxide or zinc oxide is preferred. In this embodiment the benefit is to scatter ultraviolet wavelengths of light, which are between 290 and 400 nanometers. For this purpose it is desirable to have non-visible UV scattering particles. Therefore, the desired particle size is substantially less than 200 nanometers, which scatter at least 90% of UV light in the wave lengths of from about 290 nanometers to about 400 nanometers. The preferred particle size range of titanium dioxide or zinc oxide for effective scattering of UVA and UVB wavelengths is between 10 and 100 nm.

In yet another embodiment of the present invention the particles delivered into the stratum corneum are designed to scatter little or none of the visible wavelengths of light (400-700 nm). In this embodiment the intention is to allow more visible light to penetrate through the stratum corneum. The benefit of allowing more light to transmit through the stratum corneum is to increase the perception of skin radiance. One measure of skin radiance is the amount of visible light that emanates from the skin. The amount of light that emanates from the skin is proportional to the amount of light that is allowed to enter the skin. The main barrier to light passing into the skin is the stratum corneum. As humans age the stratum corneum layers scatter more of the visible light, allowing less light to pass through the stratum corneum and thus less light to emanate from the skin. By embedding optically transparent particles into the skin the effective amount of visible light that enters the skin will be greater and thus the amount of light emanating from the skin will alos increase, thereby increasing the perceived skin radiance. Any optically transparent or translucent particle safe for contact with human skin may be used. Preferred particle size ranges are between 10 nanometers and 10 microns. The preferred level of optical transparency of the particles would allow no less than 40% of the visible wavelengths of light to pass through the particle. Materials that may be used to provide the radiance benefit include, but are not limited to: polyethylene, polypropylene, polyethylene terephthalate, polycarbonate, polyvinyl chloride, glass, and silica.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of achieving a skin benefit comprising: depositing a composition comprising particles onto mammalian skin such that when the particles contact the mammalian skin they have a momentum defined by $\rho v r$ within the range of about 0.1 kg/ms $\leq \rho v r \leq$ about 12.0 kg/ms and wherein the particles are imbedded below the first layer of dead skin cells in the stratum corneum of the skin and the particles do not pass all the way through the stratum corneum into the living cells of the epidermis or dermis layers of the skin, wherein the particles are titanium dioxide.

2. The method of claim 1, wherein the particles are in the range of from about 10 nanometers to about 10 micrometers in size.

3. The method of claim 1, wherein the particles are less than 200 nm in size and the particles scatter less than 10% of light in the wavelengths of from about 400 nanometers to about 700 nanometers.

4. The method of claim 1, the particles are from about 10 nanometers to about 100 nanometers in size and the particles scatter at least 90% of UV light in the wavelengths of from about 290 nanometers to about 400 nanometers.

5. The method of claim 1, wherein the particles are imbedded from about 10 micrometers to about 40 micrometers into the mammalian skin.

6. The method of claim 1, wherein the particles remain imbedded in the stratum corneum of the skin for at least one day.

7. The method of claim 1, wherein the skin benefit is selected from the group consisting of providing a cosmetic effect, skin protection, skin radiance, and combinations thereof.

8. A method of applying a composition onto mammalian skin: depositing a composition comprising particles onto the mammalian skin such that when the particles contact the mammalian skin they have a momentum defined by $\rho v r$ within the range of about 0.1 kg/ms $\leq \rho v r \leq$ about 12.0 kg/ms; wherein the particles are titanium dioxide.

9. The method of claim 8, wherein the particles are imbedded from about 10 micrometers to about 40 micrometers into the mammalian skin.

10. The method of claim 8 wherein the particles remain imbedded in the stratum corneum of the skin for at least one day.

11. The method of claim 9 wherein the particles are not permanently imbedded in the stratum corneum.

12. The method of claim 8 wherein the particles are deposited using a high velocity gaseous stream.

* * * * *